United States Patent [19]
Baucom et al.

[11] Patent Number: 5,334,788
[45] Date of Patent: * Aug. 2, 1994

[54] REACTION OF SUBSTRATE COMPOUNDS WITH FLUORINE IN AN EDUCTOR

[75] Inventors: Keith B. Baucom, Alachua; Adam C. Alty, Gainesville; Earl J. Kimmel, Jacksonville, all of Fla.

[73] Assignee: PCR Group, Inc., Gainesville, Fla.

[*] Notice: The portion of the term of this patent subsequent to Jan. 5, 2010 has been disclaimed.

[21] Appl. No.: 876,978

[22] Filed: May 1, 1992

Related U.S. Application Data

[63] Continuation of Ser. No. 345,588, May 1, 1989, Pat. No. 5,177,275.

[51] Int. Cl.$^5$ ............... C07C 19/08; C07C 17/20; C07C 22/00
[52] U.S. Cl. ...................... 570/175; 570/170; 570/160; 570/154; 570/153; 570/147; 570/145; 570/144; 570/143
[58] Field of Search ............. 570/175, 243, 170, 160, 570/154, 153, 147, 145, 144, 143; 562/98

[56] References Cited

U.S. PATENT DOCUMENTS

| | | | |
|---|---|---|---|
| 4,230,668 | 10/1980 | Sheely et al. | 570/243 |
| 4,261,916 | 4/1981 | Crosby | 562/98 |
| 4,265,837 | 5/1981 | Legutke et al. | 570/243 |

FOREIGN PATENT DOCUMENTS 0219823  4/1987  European Pat. Off. ............ 570/175

OTHER PUBLICATIONS

Edward A. Tyczkowski and Lucius A. Bigelow, J. Amer. Chem. Soc., 1955, 77, 3007.
Abe F. Maxwell, Fredric E. Detoro and Lucius A. Bigelow, J. Amer. Chem. Soc., 1960, 82, 5827.

*Primary Examiner*—Alan Siegel
*Attorney, Agent, or Firm*—Hedman, Gibson & Costigan

[57] ABSTRACT

Substrate compounds are reacted by passing them through an eductor with fluorine gas optionally in the presence of a liquid medium and preferably in a loop reactor with cooling means thereby providing rapid but controlled reaction suitable for industrial scale production. Vinylidene chloride, for example, smoothly produces dichlorodifluoroethane and dichlorotrifluoroethane in good yield.

11 Claims, 3 Drawing Sheets

REACTION OF SUBSTRATE COMPOUNDS WITH FLUORINE IN AN EDUCTOR

This is a continuation of application Ser. No. 07/345,588 filed May 1, 1989 now U.S. Pat. No. 5,177,275.

The present invention relates to a novel process for treating substrate compounds with fluorine. More particularly, it relates to reacting a substrate compound with elemental fluorine in an eductor, a form of a jet pump that makes use of the momentum of one fluid to move another. In comparison with the state-of-the art, the novel process of this invention is uniquely suitable for rapid treatment of substrate compounds with fluorine in a controlled manner, allowing large-scale production of valuable products.

BACKGROUND OF THE INVENTION

Prior art has previously demonstrated that reaction of substrate compounds using elemental fluorine is a highly exothermic process, making it difficult to obtain good yields of the desired products of the reaction and scale-up to industrial production. Attempts to control the reaction have involved the use of the dilute fluorine (1-20%) in an inert diluent ($N_2$, Be, Ar) at low temperature ($-70°$ C. to $-85°$ C.) and use of an inert solvent ($CFCl_3$, $CF_2Cl_2$, $CFCl_2CF_2Cl$) [Eur. Pat. Appl. No. 0 219 823 A1 dated Apr. 29, 1987; S. Rozen and C. Gal, *J. Org. Chem*, (1987), 52 2769]. Even with the use of such mild conditions, in order to control the exotherm and prevent unwanted side reactions, the rate of fluorine addition is less than 80 ml min$^{-1}$ (less than 7.6 g hr$^{-1}$), thus making large scale reactions impractical. Other techniques, such as the "LaMar" method [for example R. J. Lagow et al, *J. Org. Chem*, (1989), 54 1990] or Aersol Direct Fluorination [J. L. Adcock et al, *J. Am. Chem Soc.*, (1981), 103 6937] both involve sophisticated apparatus and low $F_2$ flow rates (less than 60 ml min$^{-1}$), again unsuitable for large-scale production. It has now been discovered that by the use of an eductor for the introduction of fluorine, preferably in a loop reactor having cooling zones, e.g., cooling coils equipped to be externally cooled, substrate compounds can be treated with fluorine rapidly in a controlled manner with fluorine rates as high as possible based on desired reaction control, thus making large-scale fluorine reaction a viable process. Substrate compounds that can be treated with fluorine by this process include, but are not limited to alkenes, cycloalkenes, alkynes, allenes, aliphatics, cycloaliphatics, aromatics, compounds with multiple bonds ($>C=N-$, $-C\equiv N$, $>=O$, etc.,) compounds of sulfur, nitrogen, phosphorus, iodine, bromine, chlorine, oxygen, silicon, and the like. Such compounds can be organic or inorganic. The term "fluorination" is used herein in its broadest sense: fluorine can react by addition, substitution, oxidation, polymerization and any other reaction where fluorine may, or may not, be present in the final product. Thus there is used the term "substrate compound" to contemplate as a starting material any compound having fluorine-reactive sites.

BRIEF DESCRIPTION OF THE DRAWINGS

The drawings are intended to facilitate understanding the invention.

SUMMARY OF THE INVENTION

According to the present invention there is provided a process comprising
 (a) reacting
  (i) a substrate compound or a mixture of such compounds having at least one site for fluorination with
  (ii) elemental fluorine, alone, or in admixture with an inert gas, in an eductor until the reaction is substantially complete; and
 (b) recovering,
  (i) a reacted substrate compound,
  (ii) a mixture of such compounds or
  (iii) an oligomeric derivative of (i) or (ii).

Preferably, the process is carried out in a loop reactor comprising cooling zones for controlling the heat of reaction with fluorine. In a preferred embodiment, the reaction temperature is from about $-80°$ C. to about $+100°$ C. The process can be carried out with a reaction mixture consisting essentially of (a)(i) and (a)(ii); alternatively, the process can be carried out with a reaction mixture comprising (a)(i), (a)(ii) and (a)(iii), a liquid medium, at a temperature of about the medium freezing point to about the medium boiling point. If a medium is used, preferably it comprises a perhalogenated organic liquid or an inorganic liquid selected from water, hydrogen fluoride, and the like, or a mixture of any of the foregoing. The invention contemplates in a preferred embodiment processes in which the substrate compound (a)(i) is capable of reacting with fluorine by (1) adding fluorine across a multiple bond; (2) replacing hydrogen by fluorine; (3) replacing halogen by fluorine; or a combination of any of (1), (2) and (3), particularly when (a)(i) comprises a halohydrocarbon or a mixture thereof.

DETAILED DESCRIPTION OF THE INVENTION

Figure 1:
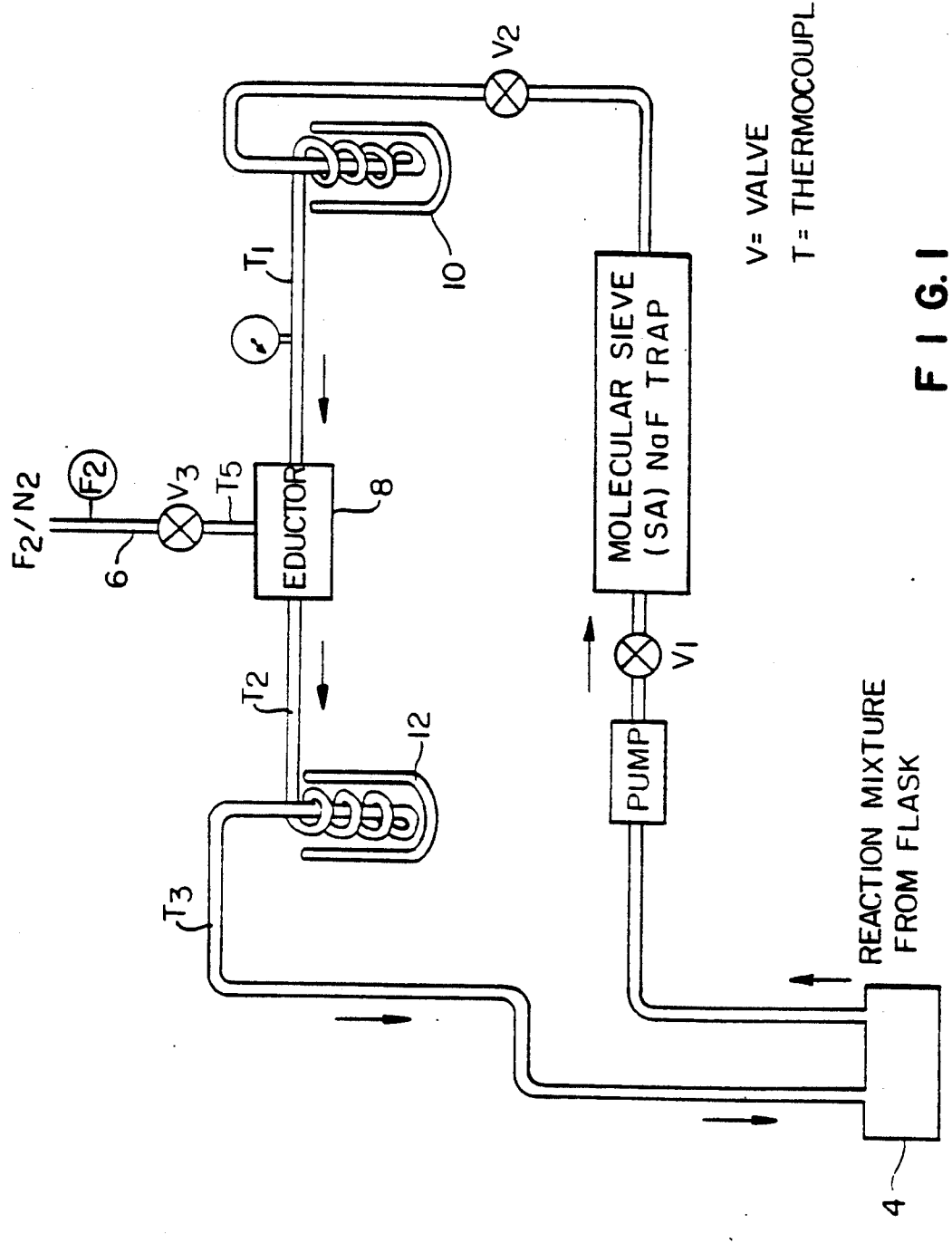
FIG. 1 represents in flow diagram form an apparatus suitable for reacting a substrate compound with fluorine by means of a loop reactor utilizing an eductor and cooling coils in accordance with the present invention.

Referring to FIG. 1, the novel process using elemental fluorine of this invention conveniently utilizes a loop reactor 2 through which is pumped from flask 4 the reaction mixture containing the substrate compound to be treated with fluorine optionally suspended or dissolved in a liquid medium ($CFCl_3$, $CF_2Cl_2$, $CCl_4$, etc) at high flows, e.g., greater than 8 l min$^{-1}$. Fluorine is introduced to the reaction mixture via the eductor 8 either undiluted (100%), or diluted with nitrogen or other inert gas as desired or as required, the total flow of gas is generally many times that which can be added without the use of this technique. The presence of eductor 8 leads to highly efficient mixing between the reaction mixture and elemental fluorine. Any resulting highly exothermic reaction is controlled, however, by passage of the circulating reaction mixture rapidly through externally cooled coils 10 and 12. Doing so will provide highly efficient cooling at the point of fluorine addition, thereby preventing hot spots and undesired side-reactions. For example; 100% fluorine can be added to selected substrate compounds, e.g., unsaturated organics, at −70° C. at the rate of 1200 ml min⁻¹ to produce the 1,2-addition product with negligible (less than 10% by-product formation). This represents a rate of fluorine addition twenty-five times greater than has been previously attainable and the use of multiple eductor/cooling coils (not shown) in the reactor loop would further greatly enhance capacity.

The system of fluorine treatment of this invention is not restricted to electrophilic fluorinations (temperature generally less than −40° C.), but it will also find application in controlled radical reactions (temperature generally more than −40° C.), because the rapid mixing and highly efficient heat transfer enable the exotherm to be easily controlled by the temperature of the circulating reaction mixture.

The eductor used in the present invention can vary broadly in structure and materials of construction without ceasing to function in the desired manner. Where corrosion is excessive, fluorine- and HF-resistant materials of construction will, of course, be selected for the eductor as well as other system components. Suitable, for example, are stainless steel, carbon steel, nickel, Monel ®, Hastelloy C ®, copper, brass, Teflon ®, and many others Alternative designs are well known to those skilled in this art and many are available commercially. Reference is made to Perry and Chilton, Chemical Engineers Handbook, 5th Edition, McGraw-Hill, 1973, 6-15.

Figure 2:
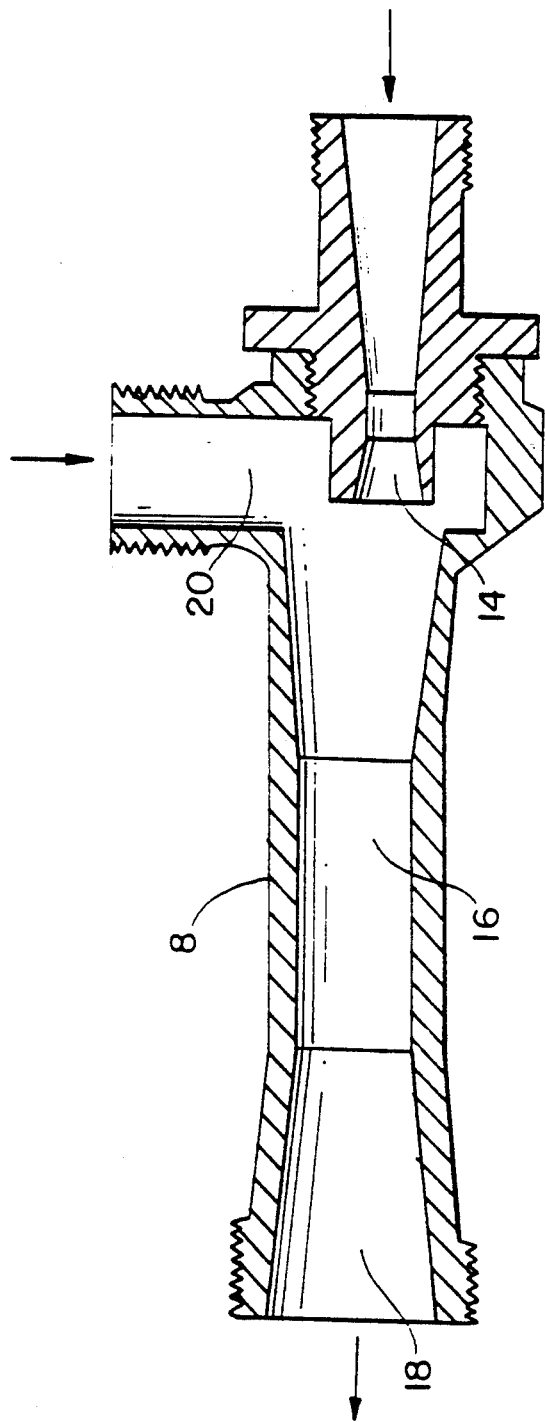
FIG. 2 is an elevated cross section showing in greater detail one type of eductor suitable for use in the apparatus shown in FIG. 1.
Figure 3:
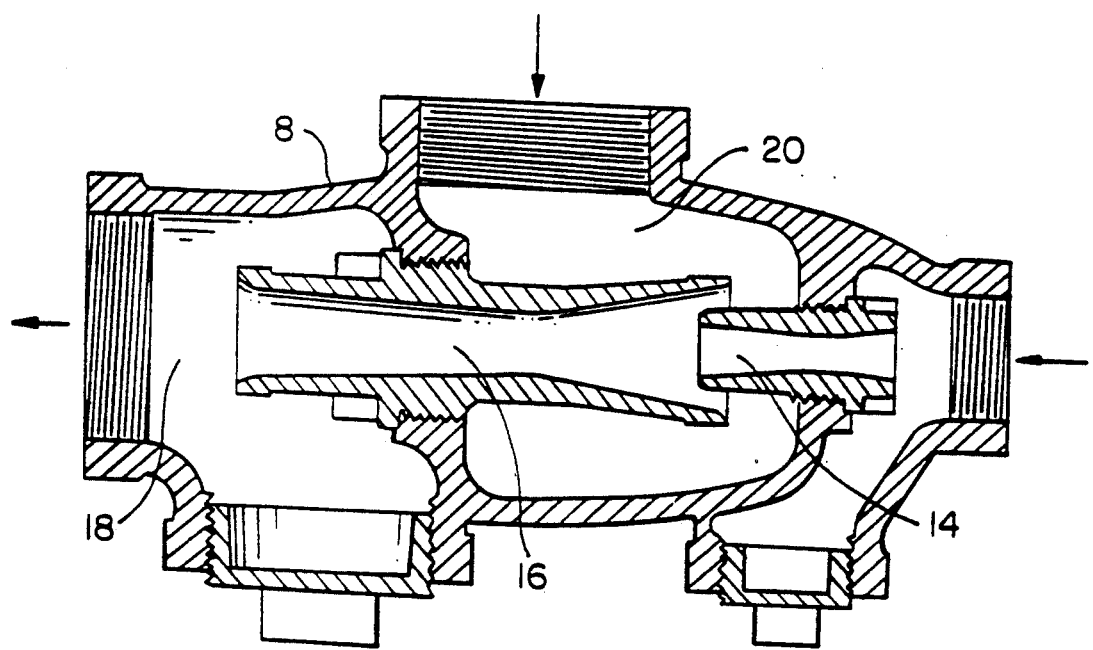
FIG. 3 is an elevated cross-section of another type of eductor suitable for use in the apparatus shown in FIG. 1.

In general, any jet pump of the ejector type can be used. Preferably, however, the pumping fluid as is shown in FIGS. 2 and 3 will enter through a nozzle and thereafter pass through a venturi nozzle 16 then out through a discharge opening 18. As the fluid passes into the venturi nozzle, it develops a suction that causes the fluorine or mixture of fluorine and any inert gas, e.g., nitrogen, in the suction chamber 20 to be entrained with the stream and be delivered through the discharge 18.

DESCRIPTION OF THE PREFERRED EMBODIMENTS

The following examples illustrate the invention but are not intended to limit the claims in any manner whatsoever.

EXAMPLE 1

A solution of vinylidene chloride (500 g) in $CFCl_3$ (15.1) was circulated through the eductor and loop as generally shown in FIG. 1 at −70° C. (all baths cooled with $CO_2$/acetone). Fluorine was introduced to the circulating liquid medium via the eductor, initially at a concentration of about 10% (91 ml min¹) in nitrogen (755 ml min⁻¹) for 30 mins, the temperature rise was controlled to −68° C., i.e., a 2° C. exotherm. During the next 60 mins., the fluorine flow was gradually increased and the nitrogen flow decreased until after 100 mins., 100% fluorine was being added at the rate of 1200 ml min⁻¹; the temperature read −63° C. at this point. Fluorination was continued for a further 90 mins. under these conditions, at which stage analysis of the reaction mixture by gas chromatography (GC) showed in addition to $CFCl_3$, $CF_2HCFCl_2$ and $CFH_{2k}$ $CFCl_2$ in a ratio of 1:3.22 with less than 10% unwanted by-products. Thus approximately 90% of the product mixture is attributable to the desired electrophilic fluorination with only a small amount of oligomeric by-products, even though 100% fluorine was used.

EXAMPLE 2

A solution of vinylidene chloride (2500 g) in $CFCl_3$ was circulated through the eductor loop shown generally in FIG. 1 at −71° C. Fluorine was introduced rapidly at the rate of 1200-1600 ml min⁻¹ such that the temperature at the eductor was 50°-100° C., but rapidly quenched to less than −60° C. by the cooling coils. Fluorination was continued under these conditions for 5 hours until approximately 50% of the vinylidene chloride had been consumed. Gas Chromatographic (GC) analysis of the reaction mixture showed no $CFH_2CFCl_2$, the product expected by addition of fluorine across the double bond; but instead, a product corresponding to a dimer, the identity of which is not clearly understood at this time, was formed in 70% yield (as calculated by GC and based on unreacted starting material). The detection of chlorine in the off-gases of the reaction was considered evidence of a free radical process.

The above-mentioned publications and patent and/or applications are incorporated herein by reference.

Many variations of the invention will suggest themselves to those skilled in the art in light of the foregoing detailed description. For example, instead of vinylidene chloride, vinyl chloride, benzene, carbon disulfide, diphenylacetylene, ethane, acetonitrile, carbon monoxide, and many others, as well as mixtures of any of them, can be used as starting materials. The reaction can be carried out in the absence of trichlorofluoromethane, or with water and/or hydrogen fluoride as liquid media. Instead of a mixture of fluorine and nitrogen, fluorine alone can be fed to the eductor or fluorine mixed with argon and the like can be fed. The cooling coils can be omitted. All such obvious variations are within the full intended scope of the appended claims.

We claim:

1. A process comprising
   (a) inducing movement in a fluid stream which is or contains a substrate compound having at least one fluorine-reactive site to provide a moving substrate stream
   (b) educting elemental fluorine, alone, or in admixture with an inert gas, into the stream of fluid substrate whereby said fluorine is reacted rapidly with said substrate in a controlled manner; and
   (c) recovering a reacted substrate compound, a mixture of such compounds or an oligomeric derivative of such compound or compounds, and
   wherein step (b) is carried out in an eductor comprising a venturi nozzle having a throat for directing the moving fluid substrate and a suction chamber for introducing fluorine upstream of said throat into said moving fluid substrate.

2. A process as defined in claim 1 carried out in a loop reactor comprising cooling zones for controlling the heat of fluorine reaction.

3. A process as defined in claim 1 wherein the reaction temperature is from about −80° C. to about +100° C.

4. A process as defined in claim 2 wherein the reaction temperature is from about −80° C. to about +100° C.

5. A process as defined in claim 1 carried out with a reaction mixture consisting essentially of said substrate compound and elemental fluorine.

6. A process as defined in claim 1 carried out with a liquid stream comprising said substrate compound, elemental fluorine, alone, or in admixture with an inert gas and a liquid medium, at a temperature of from about the medium freezing point to about the medium boiling point.

7. A process as defined in claim 6 wherein the liquid stream includes a perhalogenated organic liquid or an inorganic liquid selected from water, hydrogen fluoride or a mixture of any of the foregoing.

8. A process as defined in claim 1 wherein said substrate compound is capable of reacting with fluorine by
(1) adding fluorine across a multiple bond;
(2) replacing hydrogen by fluorine;
(3) replacing halogen by fluorine; or a combination of any of (1), (2) and (3).

9. A process as defined in claim 8 wherein said substrate compound comprises a hydrocarbon, a halohydrocarbon or a mixture thereof.

10. A process as defined in claim 1 further comprising the step of delivering the fluorine to a venturi at a location upstream of the convergent section of the venturi.

11. A process as defined in claim 10 wherein the fluorine is delivered to the venturi normal to the axis of the venturi.

* * * * *